United States Patent
Acholla et al.

(10) Patent No.: US 9,770,808 B2
(45) Date of Patent: Sep. 26, 2017

(54) METHOD OF MANUFACTURING CHEMICAL MECHANICAL POLISHING PADS

(71) Applicants: Rohm and Haas Electronic Materials CMP Holdings, Inc., Newark, DE (US); Dow Global Technologies LLC, Midland, MI (US)

(72) Inventors: Francis V. Acholla, New Castle, DE (US); Andrew Wank, Avondale, PA (US); Mark Gazze, Lincoln University, PA (US); Scott Chang, Taipei (TW); Jeff Tsai, Chunan (TW); William A. Heeschen, Midland, MI (US); James David Tate, Lake Jackson, TX (US); Leo H. Chiang, Pearland, TX (US); Swee-Teng Chin, Pearland, TX (US)

(73) Assignees: Rohm and Haas Electronic Materials CMP Holdings, Inc., Newark, DE (US); Dow Global Technologies LLC, Midland, MI (US)

(*) Notice: Subject to any disclaimer, the term of this patent is extended or adjusted under 35 U.S.C. 154(b) by 155 days.

(21) Appl. No.: 14/993,815

(22) Filed: Jan. 12, 2016

(65) Prior Publication Data
US 2017/0197295 A1    Jul. 13, 2017

(51) Int. Cl.
| | | |
|---|---|---|
| *B24D 11/00* | (2006.01) | |
| *B24D 18/00* | (2006.01) | |
| *B29C 59/02* | (2006.01) | |
| *B24B 37/22* | (2012.01) | |
| *B29C 65/48* | (2006.01) | |
| *B26D 7/10* | (2006.01) | |
| *G01N 21/95* | (2006.01) | |
| *G01N 21/88* | (2006.01) | |
| *G01N 21/94* | (2006.01) | |
| *B29L 31/00* | (2006.01) | |

(Continued)

(52) U.S. Cl.
CPC .............. *B24D 18/00* (2013.01); *B24B 37/22* (2013.01); *B24D 18/0072* (2013.01); *B26D 7/10* (2013.01); *B29C 59/02* (2013.01); *B29C 65/48* (2013.01); *G01N 21/8803* (2013.01); *G01N 21/94* (2013.01); *G01N 21/95* (2013.01); *B29K 2075/00* (2013.01); *B29K 2105/16* (2013.01); *B29K 2427/08* (2013.01); *B29K 2479/00* (2013.01); *B29L 2009/00* (2013.01); *B29L 2031/736* (2013.01); *G01N 2201/12* (2013.01)

(58) Field of Classification Search
None
See application file for complete search history.

(56) References Cited

U.S. PATENT DOCUMENTS

| | | | |
|---|---|---|---|
| 5,666,199 A * | 9/1997 | Hess | ...................... G01N 21/21 250/559.09 |
| 5,708,506 A | 1/1998 | Birang | |

(Continued)

*Primary Examiner* — Kaj K Olsen
*Assistant Examiner* — Ross J Christie
(74) *Attorney, Agent, or Firm* — Thomas S. Deibert

(57) ABSTRACT

A method of manufacturing chemical mechanical polishing pads is provided, wherein an automated inspection system is configured to detect macro inhomogeneities is skived sheets and to classify the skived sheets as either acceptable or suspect; wherein the acceptable skived sheets are further processed to form polishing layers of chemical mechanical polishing pads.

9 Claims, 4 Drawing Sheets

(51) Int. Cl.
*B29L 9/00* (2006.01)
*B29K 75/00* (2006.01)
*B29K 105/16* (2006.01)
*B29K 479/00* (2006.01)

(56) References Cited

U.S. PATENT DOCUMENTS

| | | | | |
|---|---|---|---|---|
| 5,825,028 | A | * 10/1998 | Hudson | G01N 21/9501 250/302 |
| 5,961,369 | A | 10/1999 | Bartels et al. | |
| 6,650,408 | B2 | * 11/2003 | Jun | B24B 37/013 356/237.1 |
| 7,027,640 | B2 | * 4/2006 | Park | G01N 21/94 250/559.14 |
| 7,207,862 | B2 | 4/2007 | Nabeya et al. | |
| 7,241,201 | B2 | 7/2007 | Eischeid et al. | |
| 8,011,999 | B2 | 9/2011 | Nagase et al. | |
| 2002/0036264 | A1 | * 3/2002 | Nakasuji | G01N 23/225 250/306 |
| 2004/0159787 | A1 | * 8/2004 | Nakasuji | H01J 37/28 250/311 |
| 2008/0273193 | A1 | * 11/2008 | Nishiyama | G01N 21/9501 356/73 |

* cited by examiner

METHOD OF MANUFACTURING CHEMICAL MECHANICAL POLISHING PADS

The present invention relates generally to the field of manufacture of chemical mechanical polishing pads. In particular, the present invention is directed to a method of manufacturing chemical mechanical polishing pads comprising a polishing layer.

In the fabrication of integrated circuits and other electronic devices, multiple layers of conducting, semiconducting and dielectric materials are deposited on or removed from a surface of a semiconductor wafer. Thin layers of conducting, semiconducting, and dielectric materials may be deposited by a number of deposition techniques. Common deposition techniques in modern processing include physical vapor deposition (PVD), also known as sputtering, chemical vapor deposition (CVD), plasma-enhanced chemical vapor deposition (PECVD), and electrochemical plating (ECP).

As layers of materials are sequentially deposited and removed, the uppermost surface of the wafer becomes non-planar. Because subsequent semiconductor processing (e.g., metallization) requires the wafer to have a flat surface, the wafer needs to be planarized. Planarization is useful in removing undesired surface topography and surface defects, such as rough surfaces, agglomerated materials, crystal lattice damage, scratches, and contaminated layers or materials.

Chemical mechanical planarization, or chemical mechanical polishing (CMP), is a common technique used to planarize substrates, such as semiconductor wafers. In conventional CMP, a wafer is mounted on a carrier assembly and positioned in contact with a polishing pad in a CMP apparatus. The carrier assembly provides a controllable pressure to the wafer, pressing it against the polishing pad. The pad is moved (e.g., rotated) relative to the wafer by an external driving force. Simultaneously therewith, a chemical composition ("slurry") or other polishing solution is provided between the wafer and the polishing pad. Thus, the wafer surface is polished and made planar by the chemical and mechanical action of the pad surface and slurry.

In U.S. Pat. No. 5,578,362, Reinhardt et al. disclose an exemplary polishing pad known in the art. The polishing pad of Reinhardt comprises a polymeric matrix having microspheres dispersed throughout. Generally, the microspheres are blended and mixed with a liquid polymeric material and transferred to a mold for curing. The molded article is then sliced to form polishing layers. Unfortunately, polishing layers formed in this manner may exhibit unwanted defects that may, when incorporated into a polishing pad, cause defects to a substrate polished therewith.

One asserted approach for addressing the concern regarding potential defects in the polishing layers of chemical mechanical polishing pads is disclosed by Park et al. in U.S. Pat. No. 7,027,640. Park et al. disclose an apparatus for detecting or inspecting defects on a pad for use in performing chemical mechanical polishing of a wafer, comprising: a pad driving device for loading the pad thereon and moving the pad; a camera installed to face the pad for converting an image of the pad into an electrical signal and outputting the converted electrical signal; a digital image data acquisition device for converting the electrical signal transmitted from the camera into a digital signal; and an image data processing unit for processing the image data and detecting the defects on the pad, wherein the image data processing unit calculates one or more quantitative characteristic values of light based on the image data on any one of the points which are acquired from the image data acquisition device, and determines a location on the pad, where a difference between a level value obtained by combining one or more of the acquired quantitative characteristic values and a level value obtained from a normal surface of the pad is greater than a predetermined value, as a defect.

Notwithstanding, the apparatus and method described by Park et al. are designed for the inspection of completed chemical mechanical polishing pads that are in a ready for polishing configuration using reflected light. The use of reflected light for inspecting chemical mechanical polishing pads and the polishing layers incorporated into such pads, in particular, has significant drawbacks. The use of reflected light has limited capability to identify subsurface defects in the incorporated polishing layers, which defects are not proximate to the surface of the polishing layer. Nevertheless, as a chemical mechanical polishing pad is used, the surface of the polishing layer is gradually worn down. Hence, defects that were distant from the surface of a polishing layer of a given chemical mechanical polishing pad initially, will become increasingly more proximate to the polishing surface during the useful life of the pad. Moreover, chemical mechanical polishing pads in a ready for polishing configuration conventionally include modifications to the polishing surface of the polishing layer to facilitate polishing of a substrate (e.g., grooves, perforations), which modifications complicate automated defect detection using gray scale as described by Park et al.

Accordingly, there remains a need for improved methods of manufacturing low defect, chemical mechanical polishing pads having polishing layers using automated inspection methods with enhanced polishing layer defect identification capabilities.

The present invention provides a method of manufacturing a chemical mechanical polishing pad having a polishing layer, comprising: providing a cured cake formed from a curable material; wherein the curable material comprises a liquid prepolymer and a plurality of microelements, wherein the plurality of microelements dispersed in the liquid prepolymer; skiving the cured cake to form a plurality of skived sheets; providing an automated inspection system, comprising: a magazine; a light source, which emits a beam; a light detector; a digital image data acquisition device; and, an image data processing unit; loading the plurality of skived sheets into the magazine; conveying the plurality of skived sheets, one skived sheet at a time, between the light source and the light detector; wherein the each skived sheet has a thickness, $T_S$, between a transmission surface and an impinging surface thereof; wherein the transmission surface and the impinging surface are substantially parallel; wherein the beam emitted from the light source is oriented to impinge on the impinging surface; and, wherein the light detector is oriented to detect a transmitted light from the beam that is transmitted through the thickness, $T_S$, and out the transmission surface; wherein the transmitted light has at least one detectable property; wherein the at least one detectable property includes an intensity of the transmitted light; wherein the at least one detectable property is converted into an electrical signal by the light detector; wherein the electrical signal from the light detector is converted into a digital signal by the digital image data acquisition device; wherein the digital signal from the digital image data acquisition device is processed by the image data processing unit, wherein the image data processing unit is configured to detect macro inhomogeneities and to classify skived sheets as either acceptable or suspect; wherein the plurality of skived sheets is divided into a population of acceptable sheets and a population of suspect sheets; wherein the population of acceptable sheets includes at least one acceptable sheet; and, processing an acceptable sheet from the population of acceptable sheets to form the polishing layer of the chemical mechanical polishing pad; wherein the polishing layer is adapted for polishing a substrate.

DETAILED DESCRIPTION

The method of the present invention provides significant improvement in the quality of finished (ready for use) chemical mechanical polishing pads. The method of the present invention greatly enhances the quality control aspects of chemical mechanical polishing pad production using skived sheets formed from polymeric materials containing microelements dispersed therein by performing a first inspection of the skived sheets to identify acceptable sheets from a plurality of skived sheets and mapping the transmission surfaces of suspect sheets to facilitate focused visual inspection of macro inhomogeneity containing portions of the suspect sheets. In this way, operator fatigue is greatly reduced (i.e., operators are not required to spend endless hours staring at acceptable skived sheets to locate macro inhomogeneities). Hence, enabling increased operator focus where it brings the most value (i.e., evaluating specific inhomogeneities in skived sheets to determine suitability for use).

The term "poly(urethane)" as used herein and in the appended claims encompasses (a) polyurethanes formed from the reaction of (i) isocyanates and (ii) polyols (including diols); and, (b) poly(urethane) formed from the reaction of (i) isocyanates with (ii) polyols (including diols) and (iii) water, amines or a combination of water and amines.

Figure 3:
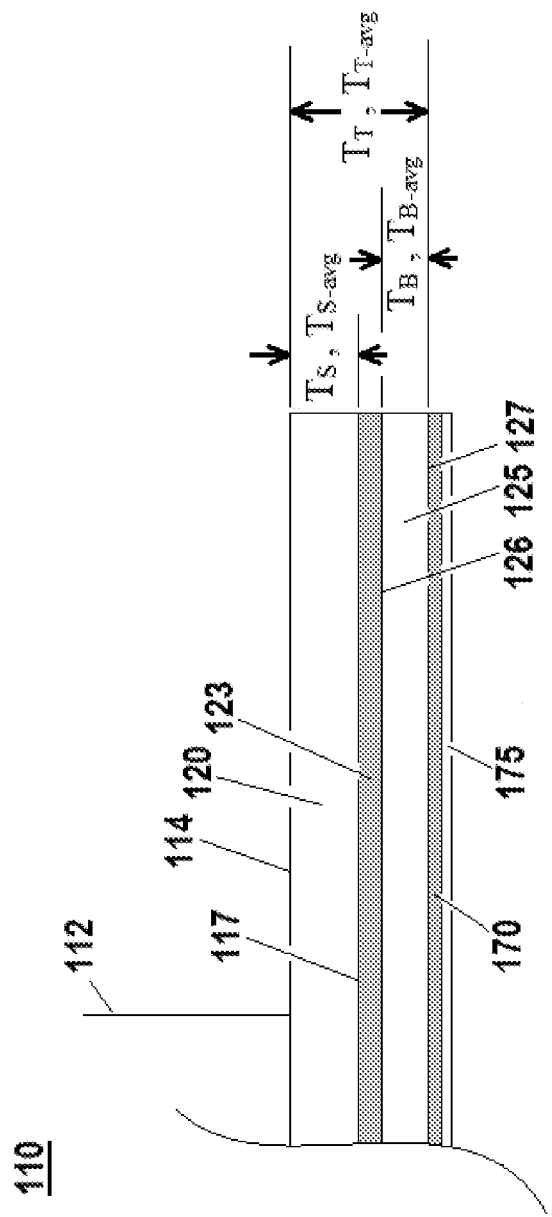
FIG. 3 is a depiction of a cross sectional cut away view of a chemical mechanical polishing pad incorporating, as a polishing layer, a skived sheet.

The term "average skived sheet thickness, $T_{S\text{-}avg}$" as used herein and in the appended claims in reference to a skived sheet (20) having a transmission surface (14) and an impinging surface (17) means the average of the thickness, $T_S$, of the skived sheet (20) measured in a direction normal to the plane (28) of the transmission surface (14) from the transmission surface (14) to the impinging surface (17) of the skived sheet (20). (See FIG. 3).

The term "average base layer thickness, $T_{B\text{-}avg}$" as used herein and in the appended claims in reference to a chemical mechanical polishing pad (110) having a subpad (125) interfaced with a skived sheet incorporated as a polishing layer (120) having a polishing surface (114) means the average of the thickness, $T_B$, of the subpad (125) measured in a direction normal to the polishing surface (114) from the bottom surface (127) of the subpad (125) to the top surface (126) of the subpad (125). (See FIG. 3).

The term "average total thickness, $T_{T\text{-}avg}$" as used herein and in the appended claims in reference to a chemical mechanical polishing pad (110) having a skived sheet incorporated as a polishing layer (120) having a polishing surface (114) means the average of the thickness, $T_T$, of the chemical mechanical polishing pad (110) measured in a direction normal to the polishing surface (114) from the polishing surface (114) to the bottom surface (127) of the subpad (125). (See FIG. 3).

Figure 1:
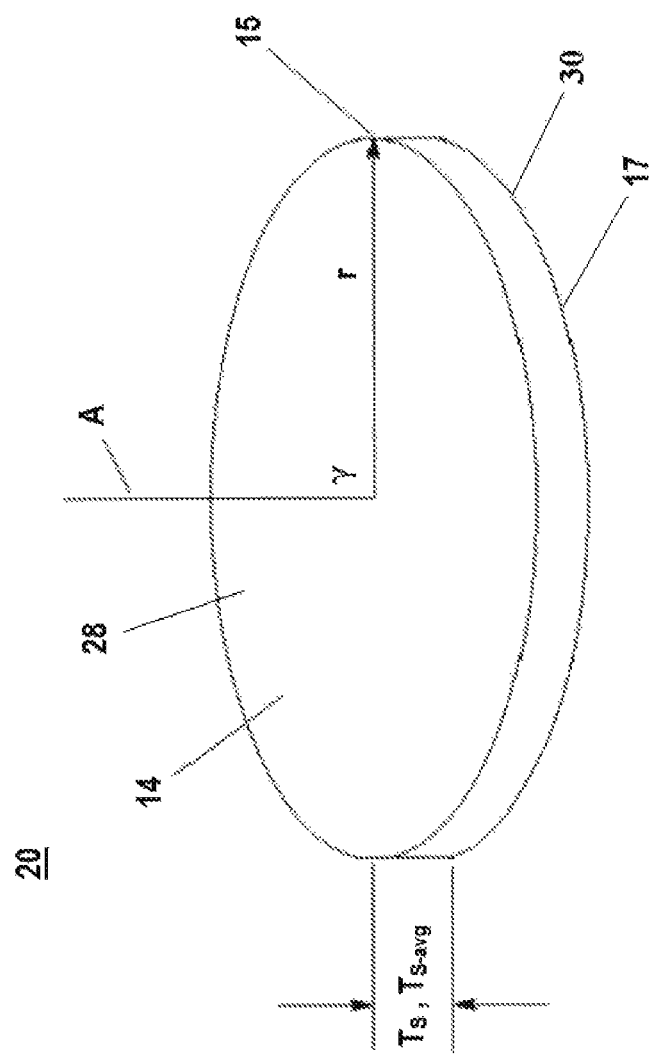
FIG. 1 is a depiction of a perspective view of a skived sheet.
Figure 2:
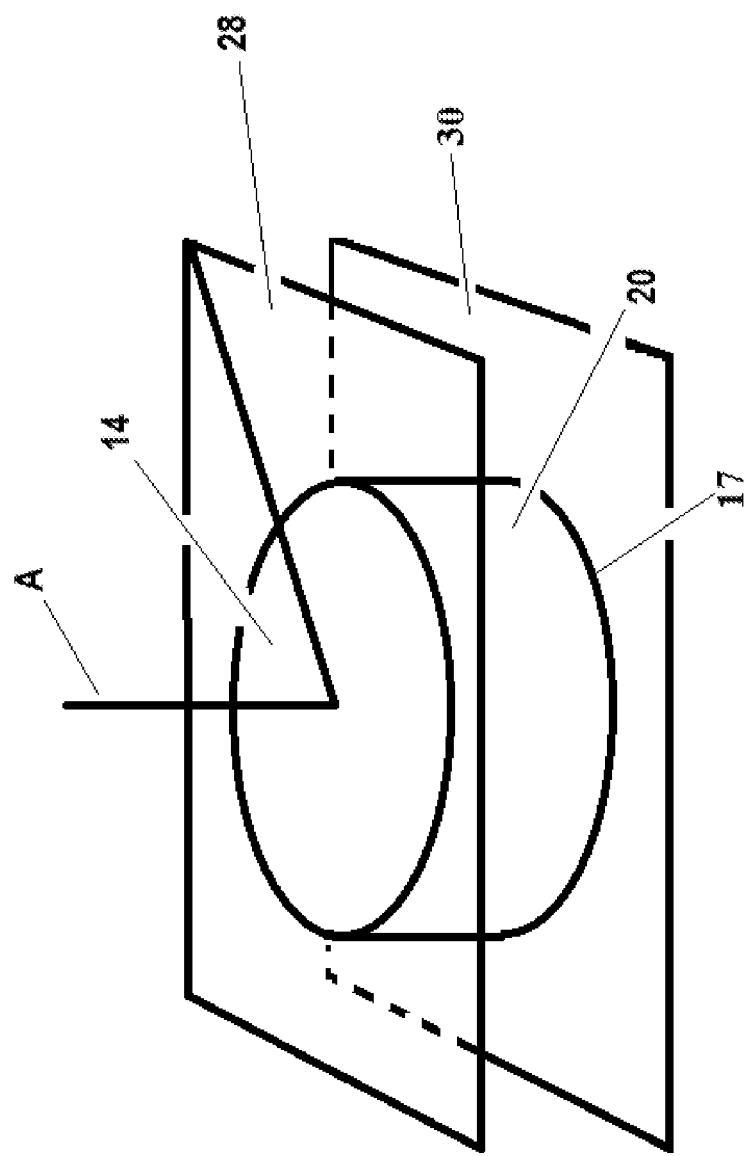
FIG. 2 is a depiction of a perspective view of a skived sheet.

The term "substantially circular cross section" as used herein and in the appended claims in reference to a skived sheet (20) means that the longest radius, r, of the skived sheet (20) projected onto the plane (28) of the transmission surface (14) of the skived sheet (20) from a central axis, A, to the outer perimeter (15) of the skived sheet (20) is ≤20% longer than the shortest radius, r, of the skived sheet (20) projected onto the plane (28) of the transmission surface (14) of the skived sheet (20) from the central axis, A, to the outer perimeter (15) of the skived sheet (20). (See FIGS. 1 & 2).

The term "substantially parallel" as used herein and in the appended claims in reference to a skived sheet (20) means that the central axis, A, (and any lines parallel therewith) normal to a plane (30) of the impinging surface (17) of the skived sheet (20) will intersect a plane (28) of the transmission surface (14) at an angle, γ; wherein the angle, γ, is between 89 and 91°. (See FIGS. 1 & 2).

Figure 4:
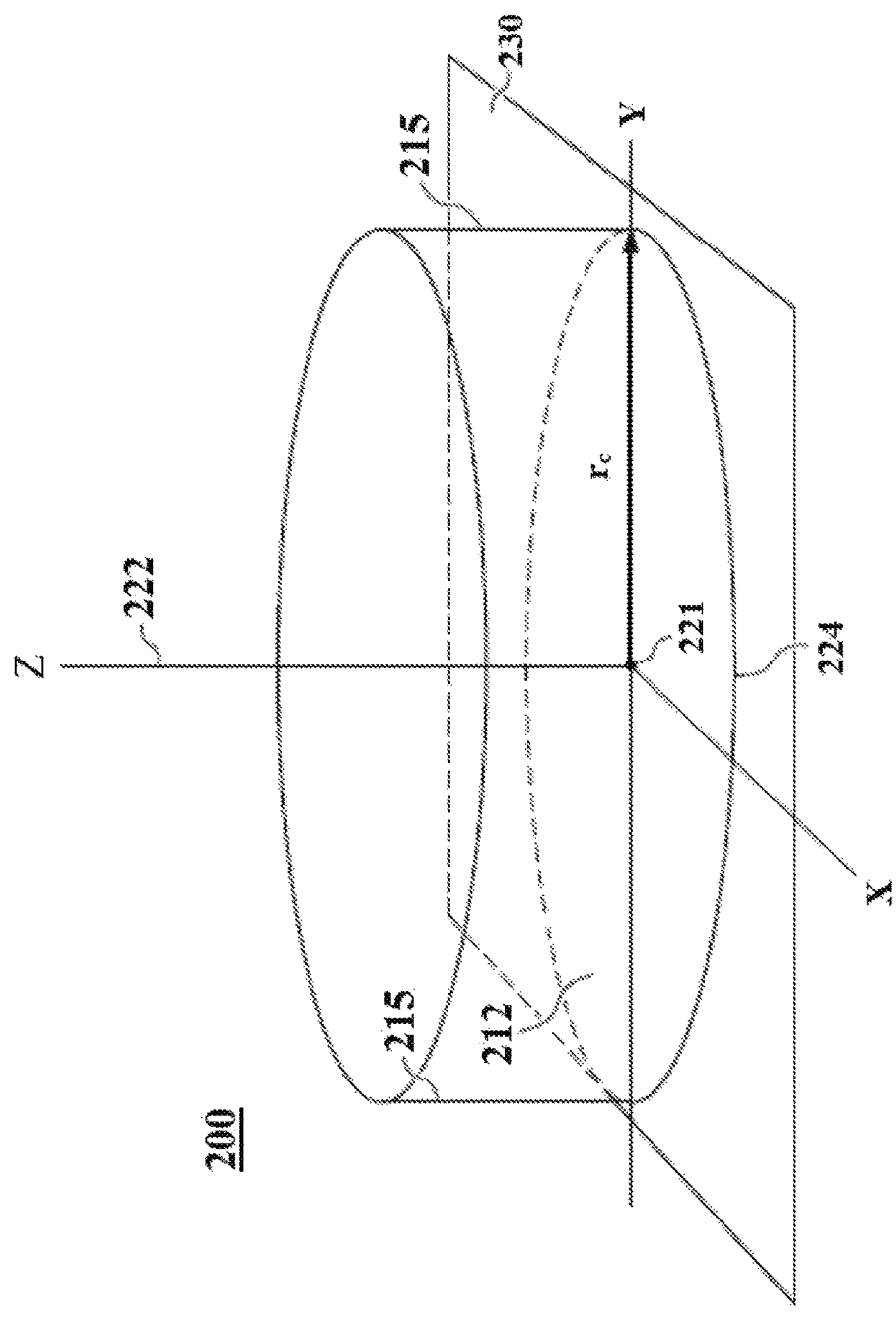
FIG. 4 is a depiction of a perspective view of a mold cavity.

The term "substantially perpendicular" as used herein and in the appended claims in reference to a mold cavity (200) means that the vertical internal boundary (215) rises from the bottom internal boundary (212) at an angle of 85 and 95° relative to the x-y plane (230). (See FIG. 4).

The term "macro inhomogeneity" as used herein and in the appended claims means a localized region on the transmission surface of a skived sheet surrounded by an adjacent region on the transmission surface of the skived sheet, wherein the detected intensity of light transmitted through the localized region is higher or lower than the detected intensity of light transmitted through the adjacent region by an amount of ≥0.1% of the detectable intensity range of the light detector; and, wherein the localized region encompasses a portion of the transmission surface large enough to occlude a circle having a diameter of 15.875 mm in the plane of the transmission surface.

The term "density defect" as used herein and in the appended claims refers to a macro inhomogeneity in a skived sheet with a significantly reduced microelement concentration relative to the surrounding region of the skived sheet. Density defects exhibit a markedly higher transparency (i.e., higher detected intensity of light transmitted) compared with the surrounding region of the skived sheet.

The term "air hole" as used herein and in the appended claims refers to a macro inhomogeneity in a skived sheet with an air inclusion resulting in a markedly higher transparence (i.e., higher detected intensity of light transmitted) compared with the surrounding region of the skived sheet.

The term "inclusion defect" as used herein and in the appended claims refers to a macro inhomogeneity in a skived sheet with a foreign contaminant resulting in a markedly lower transparence (i.e., lower detected intensity of light transmitted) compared with the surrounding region of the skived sheet.

Preferably, the method of manufacturing a chemical mechanical polishing pad having a polishing layer of the present invention, comprises: providing a cured cake formed from a curable material; wherein the curable material comprises a liquid prepolymer and a plurality of microelements, wherein the plurality of microelements dispersed in the liquid prepolymer; skiving the cured cake to form a plurality of skived sheets; providing an automated inspection system, comprising: a magazine (preferably, wherein the magazine has a capacity for holding at least 10 skived sheets; more preferably, at least 15 skived sheets; still more preferably, at least 20 skived sheets; most preferably, at least 30 skived sheets); a light source, which emits a beam; a light detector; a digital image data acquisition device; and, an image data processing unit; loading the plurality of skived sheets into the magazine; conveying the plurality of skived sheets, one skived sheet at a time, between the light source and the light detector; wherein the each skived sheet has a thickness, $T_S$, between a transmission surface and an impinging surface thereof; wherein the transmission surface and the impinging surface are substantially parallel; wherein the beam emitted from the light source is oriented to impinge on the impinging surface; and, wherein the light detector is oriented to detect a transmitted light from the beam that is transmitted through the thickness, $T_S$, and out the transmission surface (preferably, wherein the beam emitted from the light source impinges on each skived sheet normal to the impinging surface thereof); wherein the transmitted light has at least one detectable property; wherein the at least one detectable property includes an intensity of the transmitted light (preferably, wherein the at least one detectable property further includes a wavelength spectrum of the transmitted light); wherein the intensity of the transmitted light is converted into an electrical signal by the light detector; wherein the electrical signal from the light detector is converted into a digital signal by the digital image data acquisition device; wherein the digital signal from the digital image data acquisition device is processed by the image data processing unit, wherein the image data processing unit is configured to detect macro inhomogeneities and to classify skived sheets as either acceptable or suspect (preferably, wherein the classification is performed based on a menu of quality control criteria); wherein the plurality of skived sheets is divided into a population of acceptable sheets and a population of suspect sheets; wherein the population of acceptable sheets includes at least one acceptable sheet; and, processing an acceptable sheet from the population of acceptable sheets to form the polishing layer of the chemical mechanical polishing pad; wherein the polishing layer is adapted for polishing a substrate.

Preferably, the cured cake used in the method of the present invention is prepared in a mold having a mold cavity (200) defined by a bottom internal boundary (212) and a vertical internal boundary (215). (See, e.g., FIG. 4). Preferably, the bottom internal boundary (212) lies in an x-y plane (230) and the vertical internal boundary (215) is substantially perpendicular to the x-y plane (230).

Preferably, the mold cavity (200) has a central axis, $C_{axis}$, (222) that coincides with the z-axis and that intersects the bottom internal boundary (212) of the mold cavity (200) at a center point (221). Preferably, the center point (221) is located at the geometric center of the cross section, $C_{x-sect}$, (224) of the mold cavity (200) projected onto the x-y plane (230). (See, FIG. 4).

The mold cavity's cross section, $C_{x-sect}$, (224) projected onto the x-y plan (230) can be any regular or irregular two dimensional shape. Preferably, the mold cavity's cross section, $C_{x-sect}$, is selected from a polygon and an ellipse. More preferably, the mold cavity's cross section, $C_{x-sect}$, (224) is a substantially circular cross section having an average radius, $r_C$ (preferably, wherein $r_C$ is 20 to 100 cm; more preferably, wherein $r_C$ is 25 to 65 cm; most preferably, wherein $r_C$ is 40 to 60 cm). Most preferably, the mold cavity approximates a right cylindrically shaped region having a substantially circular cross section, $C_{x-sect}$, (224); wherein the mold cavity has an axis of symmetry, $C_{x-sym}$, which coincides with the mold cavity's central axis, $C_{axis}$; wherein the right cylindrically shaped region has a cross sectional area, $C_{x-area}$, defined as follows:

$$C_{x-area} = \pi r_C^2$$

wherein $r_C$ is the average radius of the mold cavity's cross sectional area, $C_{x-area}$, projected onto the x-y plane; and wherein $r_C$ is 20 to 100 cm (more preferably 25 to 65 cm; most preferably 40 to 60 cm).

Preferably, the curable material used to provide the cured cake in the method of the present invention, comprises a liquid prepolymer and a plurality of microelements, wherein the plurality of microelements are dispersed in the liquid prepolymer. Preferably, the curable material comprises a liquid prepolymer and a plurality of microelements, wherein the plurality of microelements are uniformly dispersed in the liquid prepolymer.

Preferably, the liquid prepolymer polymerizes (i.e., cures) to form a material selected from poly(urethane), polysulfone, polyether sulfone, nylon, polyether, polyester, polystyrene, acrylic polymer, polyurea, polyamide, polyvinyl chloride, polyvinyl fluoride, polyethylene, polypropylene, polybutadiene, polyethylene imine, polyacrylonitrile, polyethylene oxide, polyolefin, poly(alkyl)acrylate, poly(alkyl) methacrylate, polyamide, polyether imide, polyketone, epoxy, silicone, polymer formed from ethylene propylene diene monomer, protein, polysaccharide, polyacetate and a combination of at least two of the foregoing. Preferably, the liquid prepolymer polymerizes to form a material comprising a poly(urethane). More preferably, the liquid prepolymer polymerizes to form a material comprising a polyurethane. Most preferably, the liquid prepolymer polymerizes (cures) to form a polyurethane.

Preferably, the liquid prepolymer comprises a polyisocyanate-containing material. More preferably, the liquid prepolymer comprises the reaction product of a polyisocyanate (e.g., diisocyanate) and a hydroxyl-containing material.

Preferably, the polyisocyanate is selected from methylene bis 4,4'-cyclohexyl-isocyanate; cyclohexyl diisocyanate; isophorone diisocyanate; hexamethylene diisocyanate; propylene-1,2-diisocyanate; tetramethylene-1,4-diisocyanate; 1,6-hexamethylene-diisocyanate; dodecane-1,12-diisocyanate; cyclobutane-1,3-diisocyanate; cyclohexane-1,3-diisocyanate; cyclohexane-1,4-diisocyanate; 1-isocyanato-3,3,5-trimethyl-5-isocyanatomethylcyclohexane; methyl cyclohexylene diisocyanate; triisocyanate of hexamethylene diisocyanate; triisocyanate of 2,4,4-trimethyl-1,6-hexane diisocyanate; urtdione of hexamethylene diisocyanate; ethylene diisocyanate; 2,2,4-trimethylhexamethylene diisocyanate; 2,4,4-tri-methylhexamethylene diisocyanate; dicyclohexylmethane diisocyanate; and combinations thereof. Most preferably, the polyisocyanate is aliphatic and has less than 14 percent unreacted isocyanate groups.

Preferably, the hydroxyl-containing material used with the present invention is a polyol. Exemplary polyols include, for example, polyether polyols, hydroxy-terminated polybutadiene (including partially and fully hydrogenated derivatives), polyester polyols, polycaprolactone polyols, polycarbonate polyols, and mixtures thereof.

Preferred polyols include polyether polyols. Examples of polyether polyols include polytetramethylene ether glycol ("PTMEG"), polyethylene propylene glycol, polyoxypropylene glycol, and mixtures thereof. The hydrocarbon chain can have saturated or unsaturated bonds and substituted or unsubstituted aromatic and cyclic groups. Preferably, the polyol of the present invention includes PTMEG. Suitable polyester polyols include, but are not limited to, polyethylene adipate glycol; polybutylene adipate glycol; polyethylene propylene adipate glycol; o-phthalate-1,6-hexanediol; poly(hexamethylene adipate) glycol; and mixtures thereof. The hydrocarbon chain can have saturated or unsaturated bonds, or substituted or unsubstituted aromatic and cyclic groups. Suitable polycaprolactone polyols include, but are not limited to, 1,6-hexanediol-initiated polycaprolactone; diethylene glycol initiated polycaprolactone; trimethylol propane initiated polycaprolactone; neopentyl glycol initiated polycaprolactone; 1,4-butanediol-initiated polycaprolactone; PTMEG-initiated polycaprolactone; and mixtures thereof. The hydrocarbon chain can have saturated or unsaturated bonds, or substituted or unsubstituted aromatic and cyclic groups. Suitable polycarbonates include, but are not limited to, polyphthalate carbonate and poly(hexamethylene carbonate) glycol.

Preferably, the plurality of microelements are selected from entrapped gas bubbles, hollow core polymeric materials (i.e., microspheres), liquid filled hollow core polymeric materials, water soluble materials (e.g., cyclodextrin) and an insoluble phase material (e.g., mineral oil). Preferably, the plurality of microelements are microspheres, such as, polyvinyl alcohols, pectin, polyvinyl pyrrolidone, hydroxyethylcellulose, methylcellulose, hydropropylmethylcellulose, carboxymethylcellulose, hydroxypropylcellulose, polyacrylic acids, polyacrylamides, polyethylene glycols, polyhydroxyetheracrylites, starches, maleic acid copolymers, polyethylene oxide, polyurethanes, cyclodextrin and combinations thereof (e.g., Expancel™ from Akzo Nobel of Sundsvall, Sweden). The microspheres can be chemically modified to change the solubility, swelling and other properties by branching, blocking, and crosslinking, for example. Preferably, the microspheres have a mean diameter that is less than 150 µm, and more preferably a mean diameter of less than 50 µm. Most Preferably, the microspheres 48 have a mean diameter that is less than 15 µm. Note, the mean diameter of the microspheres can be varied and different sizes or mixtures of different microspheres 48 can be used. A most preferred material for the microspheres is a copolymer of acrylonitrile and vinylidene chloride (e.g., Expancel® available from Akzo Nobel).

The liquid prepolymer used in the method of the present invention, optionally further comprises a curing agent. Preferred curing agents include diamines. Suitable polydiamines include both primary and secondary amines. Preferred polydiamines include, but are not limited to, diethyl toluene diamine ("DETDA"); 3,5-dimethylthio-2,4-toluenediamine and isomers thereof; 3,5-diethyltoluene-2,4-diamine and isomers thereof (e.g., 3,5-diethyltoluene-2,6-diamine); 4,4'-bis-(sec-butylamino)-diphenylmethane; 1,4-bis-(sec-butylamino)-benzene; 4,4'-methylene-bis-(2-chloroaniline); 4,4'-methylene-bis-(3-chloro-2,6-diethylaniline) ("MCDEA"); polytetramethyleneoxide-di-p-aminobenzoate; N,N'-dialkyldiamino diphenyl methane; p,p'-methylene dianiline ("MDA"); m-phenylenediamine ("MPDA"); methylene-bis 2-chloroaniline ("MBOCA"); 4,4'-methylene-bis-(2-chloroaniline) ("MOCA"); 4,4'-methylene-bis-(2,6-diethylaniline) ("MDEA"); 4,4'-methylene-bis-(2,3-dichloroaniline) ("MDCA"); 4,4'-diamino-3,3'-diethyl-5,5'-dimethyl diphenylmethane, 2,2',3,3'-tetrachloro diamino diphenylmethane; trimethylene glycol di-p-aminobenzoate; and mixtures thereof. Preferably, the diamine curing agent is selected from 3,5-dimethylthio-2,4-toluenediamine and isomers thereof.

Curing agents can also include diols, triols, tetraols and hydroxy-terminated curatives. Suitable diols, triols, and tetraol groups include ethylene glycol; diethylene glycol; polyethylene glycol; propylene glycol; polypropylene glycol; lower molecular weight polytetramethylene ether glycol; 1,3-bis(2-hydroxyethoxy) benzene; 1,3-bis-[2-(2-hydroxyethoxy) ethoxy]benzene; 1,3-bis-{2-[2-(2-hydroxyethoxy) ethoxy]ethoxy}benzene; 1,4-butanediol; 1,5-pentanediol; 1,6-hexanediol; resorcinol-di-(beta-hydroxyethyl) ether; hydroquinone-di-(beta-hydroxyethyl) ether; and mixtures thereof. Preferred hydroxy-terminated curatives include 1,3-bis(2-hydroxyethoxy) benzene; 1,3-bis-[2-(2-hydroxyethoxy) ethoxy]benzene; 1,3-bis-{2-[2-(2-hydroxyethoxy) ethoxy]ethoxy}benzene; 1,4-butanediol; and mixtures thereof. The hydroxy-terminated and diamine curatives can include one or more saturated, unsaturated, aromatic, and cyclic groups. Additionally, the hydroxy-terminated and diamine curatives can include one or more halogen groups.

Preferably, in the method of the present invention, the cured cake is skived into a plurality of skived sheets of desired thickness using a skiver blade having a cutting edge. Preferably, a stropping compound is applied to the cutting edge of the skiver blade, and a strop is used to hone the cutting edge before skiving the cake into the plurality of skived sheets. Stropping compound used in the method of the present invention preferably comprises an aluminum oxide abrasive dispersed in a fatty acid. More preferably, the stropping compound used in the method of the present invention comprises 70 to 82 wt % aluminum oxide abrasive dispersed in 18 to 35 wt % fatty acid. The strop used in the method of the present invention is preferably a leather strop. Most preferably, the strop used in the method of the present invention is a leather strop designed for use with a rotary tool (e.g., Dremel® rotary tool).

Preferably, in the method of the present invention, the cured cake is heated to facilitate the skiving operation. Preferably, the cured cake is heated using infrared heating lamps during the skiving operation in which the cured cake is skived into a plurality of skived sheets.

Preferably, in the method of the present invention, the cured cake is skived such that a plurality of skived sheets are formed, wherein the average thickness of the skived sheets, $T_{S-avg}$, is 500 to 5,000 µm (preferably, 750 to 4,000 µm; more preferably, 1,000 to 3,000 µm; most preferably, 1,200 to 2,100 µm).

Preferably, in the method of the present invention, the automated inspection system comprises a magazine designed to hold, store and dispense skived sheets. Preferably, the magazine has a design capacity for holding at least 10 skived sheets (more preferably, at least 15 skived sheets; still more preferably, at least 20 skived sheets; most preferably, at least 30 skived sheets). The magazine design capacity enables an operator to load a number of skived sheets into the automated inspection system. Once the plurality of skived sheets are loaded into the magazine, the operator is able to then perform other tasks while the automated inspection system processes and classifies the plurality of skived sheets as either acceptable or suspect.

Preferably, in the method of the present invention, the automated inspection system comprises a mechanism for transferring skived sheets from the magazine, one at a time; conveying the skived sheets, one at a time, between the light source and the light detector; and, returning the skived sheets, one at a time, back into the magazine. Preferably, the mechanism includes at least one linear motor. More preferably, the mechanism includes at least one liner motor having a linear scale resolution of ≤1 µm.

Preferably, in the method of the present invention, the automated inspection system comprises a light source, which emits a beam. Preferably, the beam emitted by the light source exhibits an emission spectrum including wavelengths in the visible, ultraviolet and infrared regions. The light source can be a broad band source (e.g., a white light source) or a narrow band source (e.g., a narrow band blue light source). Preferably, the light source is a narrow band blue light source. More preferably, the light source is a narrow band blue light source, wherein the beam exhibits an emission spectrum having a peak wavelength of 460 to 490 nm (preferably, 460 to 480 nm; more preferably, 460 to 470; most preferably, 463 to 467 nm) and a full width at half max, FWHM, of ≤50 nm (preferably, ≤40 nm; more preferably, ≤35 nm; most preferably, ≤30 nm). One or ordinary skill in the art will be able to select an appropriate light source for providing a beam with an emission spectrum in the desired region. Preferably, in the method of the present invention, the automated inspection system comprises a light source, wherein the light source is a light emitting diode.

Preferably, in the method of the present invention, the automated inspection system comprises a light detector capable of converting the at least one detectable property of the transmitted light from the beam that is transmitted through the thickness, $T_S$, and out the transmission surface of a skived sheet. More preferably, in the method of the present invention, the automated inspection system comprises a light detector capable of converting an intensity of the transmitted light from the beam that is transmitted through the thickness, $T_S$, and out the transmission surface of a skived sheet. Most preferably, in the method of the present invention, the automated inspection system comprises a light detector capable of converting an intensity and a wavelength spectrum of the transmitted light from the beam that is transmitted through the thickness, $T_S$, and out the transmission surface of a skived sheet. Preferably, the light detector is an optoelectric converting device, which converts the at least one detectable property of the transmitted light incident thereon into an electric signal. Preferably, the light detector is an array of charge coupled devices (CCDs). Preferably, the charge coupled devices (CCDs) used are selected from monochromatic and color CCDs. More preferably, the light detector comprises an array of at least 5 (most preferably, at least 8) optoelectric converting devices. Most preferably, the light detector comprises an array of at least 8 charge coupled devices (CCD) image sensors having a resolution of ≤20 μm (preferably, ≤16 μm) and a field of view of ≥100 mm (preferably, ≥120 mm).

The digital image data acquisition device converts to a digital signal the electrical signal output from the light detector. Digital image data acquisition devices suitable for use with the present invention are well known in the art.

The heterogeneous compositional nature of skived sheets from a cake of polymeric material containing a plurality of microelements makes reference to a hypothetical standard sheet impractical. That is, the existence of various, innocuous production artifacts in such skived sheets make simple grayscale comparison to a standard value ineffective for use in an automated system for inspecting skived sheets for incorporation as a polishing layers in chemical mechanical polishing pads.

General purpose and specialty purpose image data processing units suitable for use with the present invention are well known in the art. Preferably, the image data processing unit in the automated inspection system used in the method of the present invention, comprises a central processing unit coupled to a non-volatile data storage unit.

Preferably, the central processing unit is further coupled to one or more user input interface controllers (e.g., mouse, keyboard) and at least one output display.

Preferably, image data processing unit is configured to detect macro inhomogeneities in the skived sheets and to classify the skived sheets as either acceptable or suspect. Preferably, the classification of the skived sheets as acceptable or suspect is performed by the image data processing unit based on a menu of quality control criteria. A variety of defects can occur during the manufacture of the skived sheets including, for example, density defects, air hole defects and inclusion defects. Note that any one or a combination of these defects can constitute a macro inhomogeneity in a skived sheet depending on the size of the affected portion of the transmission surface. Note that the various defect types will present differently to the light detector. For density defects and air holes, the defective region will be more transparent than the surrounding region of the skived sheet. For inclusion defects, the defective region will be less transparent than the surrounding region of the skived sheet. Whether such defects are acceptable depends on a number of conditions, including, for example, the substrate for which the chemical mechanical polishing pad incorporating the skived sheet will be tasked for polishing. Certain substrates are more delicate than others, and hence require tighter controls on the homogeneity of the skived sheets to be used as polishing layers in chemical mechanical polishing pads manufactured for their polishing.

Preferably, in the method of the present invention, processing the at least one acceptable sheet to form the polishing layer (120) of the chemical mechanical polishing pad (110); wherein the polishing layer (120) is adapted for polishing a substrate, comprises: forming a polishing surface (114) by at least one of (a) machining at least one groove into the acceptable sheet to form a groove pattern and (b) forming perforations that extend at least part way through the thickness, $T_s$, of the acceptable sheet. More preferably, in the method of the present invention, processing the at least one acceptable sheet to form the polishing layer (120) of the chemical mechanical polishing pad (110); wherein the polishing layer (120) is adapted for polishing a substrate, comprises forming a polishing surface (114) by machining at least one groove into the acceptable sheet to form a groove pattern. Most preferably, in the method of the present invention, processing the at least one acceptable sheet to form the polishing layer (120) of the chemical mechanical polishing pad (110); wherein the polishing layer (120) is adapted for polishing a substrate, comprises forming a polishing surface (114) by machining at least one groove into the acceptable sheet to form a groove pattern; wherein the groove pattern is adapted for polishing the substrate. (See FIG. 3).

Preferably, the chemical mechanical polishing pad (110) manufactured using the method of the present invention is preferably adapted for rotation about a central axis (112). (See FIG. 3). Preferably, the at least one groove is arranged to form a polishing surface (114) such that upon rotation of the pad (110) about the central axis (112) during polishing, at least one groove sweeps over the substrate. Preferably, the at least one groove is selected from curved grooves, linear grooves and combinations thereof. Preferably, the at least one groove exhibit a depth of ≥10 mils (preferably, 10 to 150 mils). Preferably, the at least one groove forms a groove pattern that comprises at least two grooves having a combination of a depth selected from ≥10 mils, ≥15 mils and 15 to 150 mils; a width selected from ≥10 mils and 10 to 100 mils; and a pitch selected from ≥30 mils, ≥50 mils, 50 to 200 mils, 70 to 200 mils, and 90 to 200 mils.

Preferably, the skived sheet incorporated as polishing layer (120) into the chemical mechanical polishing pad (110) contains <1 ppm abrasive particles incorporated therein.

Preferably, wherein processing the acceptable sheet, further comprises: providing a subpad (125) having a top surface (126) and a bottom surface (127); providing an adhesive (123)(preferably, wherein the adhesive is selected from at least one of a pressure sensitive adhesive, a hot melt adhesive and a contact adhesive; more preferably wherein the adhesive is selected from a pressure sensitive adhesive and a hot melt adhesive; most preferably, wherein the adhesive is a hot melt adhesive); and, laminating the top surface (126) of the subpad (125) to the base surface (117) of the polishing layer (120) using the adhesive (123). (See FIG. 3).

Preferably, in the method of the present invention, processing the at least one acceptable sheet to form the polishing layer (120) of the chemical mechanical polishing pad (110); wherein the polishing layer (120) is adapted for polishing a substrate, further comprises: providing a pressure sensitive platen adhesive layer (170) applied to the bottom surface (127) of the subpad (125).

Preferably, in the method of the present invention, processing the at least one acceptable sheet to form the polishing layer (120) of the chemical mechanical polishing pad (110); wherein the polishing layer (120) is adapted for polishing a substrate, further comprises: providing a pressure sensitive platen adhesive layer (170) applied to the bottom surface (127) of the subpad (125); and, providing a release liner (175) applied over the pressure sensitive platen adhesive layer (170), wherein the pressure sensitive platen adhesive layer (170) is interposed between the bottom surface (127) of the subpad (125) and the release liner (175). (See FIG. 3).

The incorporation of a subpad (125) into a chemical mechanical polishing pad (110) of the present invention is desirable for a certain polishing applications. One of ordinary skill in the art will know to select an appropriate material of construction and subpad thickness, $T_B$, for the subpad (125) for use in the intended polishing process. Preferably, the subpad (150) has an average subpad thickness, $T_{B-avg}$, of ≥15 mils (more preferably, 30 to 100 mils; most preferably 30 to 75 mils).

Preferably the adhesive (123) is selected from the group consisting of a pressure sensitive adhesive, a hot melt adhesive, a contact adhesive and combinations thereof. More preferably, the adhesive (123) is selected from the group consisting of a pressure sensitive adhesive and a hot melt adhesive. Most preferably, the adhesive (123) is a reactive hot melt adhesive.

Preferably, in the method of the present invention, processing the at least one acceptable sheet to form the polishing layer (120) of the chemical mechanical polishing pad (110); wherein the polishing layer (120) is adapted for polishing a substrate, further comprises: providing at least one additional layer (not shown) interfaced with and interposed between the polishing layer (120) and the pressure sensitive platen adhesive layer (170). The at least one additional layer (not shown) can be incorporated into the chemical mechanical polishing pad (110) using an additional layer adhesive (not shown). The additional layer adhesive can be selected from pressure sensitive adhesives, hot melt adhesives, contact adhesives and combinations thereof. Preferably, the additional layer adhesive is a hot melt adhesive or a pressure sensitive adhesive. More preferably, the additional layer adhesive is a hot melt adhesive.

Preferably, the chemical mechanical polishing pad (110) of the present invention is specifically designed to facilitate the polishing of a substrate selected from at least one of a magnetic substrate, an optical substrate and a semiconductor substrate. Preferably, the skived sheet incorporated as polishing layer (120) into the chemical mechanical polishing pad (110) is adapted for polishing a substrate selected from at least one of a magnetic substrate, an optical substrate and a semiconductor substrate (more preferably, a semiconductor substrate; most preferably, a semiconductor wafer).

In the method of the present invention, wherein the population of suspect sheets includes at least one suspect sheet and wherein the at least one suspect sheet contains at least one detected macro inhomogeneity; the image data processing unit is preferably further configured to produce and store in a nonvolatile memory a map of the at least one suspect sheet, wherein a location for the at least one detected macro inhomogeneity is positioned.

Preferably, the method of the present invention, further comprises: choosing a select sheet from the population of suspect sheets; wherein the population of suspect sheets includes at least one suspect sheet and wherein the at least one suspect sheet contains at least one detected macro inhomogeneity; the image data processing unit is preferably further configured to produce and store in a nonvolatile memory a map of the at least one suspect sheet, wherein a location for the at least one detected macro inhomogeneity is positioned.

Preferably, the method of the present invention, further comprises: choosing a select sheet from the population of suspect sheets; wherein the population of suspect sheets includes at least one suspect sheet and wherein the at least one suspect sheet contains at least one detected macro inhomogeneity; the image data processing unit is preferably further configured to produce and store in a nonvolatile memory a map of the at least one suspect sheet, wherein a location for the at least one detected macro inhomogeneity is positioned; and, wherein the automated inspection system, further comprises: a display; wherein an image of the select sheet is displayed on the display. The image displayed of the select sheet on the display can be an image of the entirety of the transmission surface of the select sheet. Preferably, the image of the select sheet is a partial image showing a magnification of at least one detected macro inhomogeneity. Preferably, the partial image of the select sheet displayed on the display includes the entirety of the macro inhomogeneity and the surrounding region of the transmission surface of the select sheet. Preferably, the partial image of the select sheet displayed on the display can be magnified to enhance the detail of the displayed image to facilitate a visual inspection of the select sheet. Preferably, the method of the present invention, further comprises: performing a visual inspection of the select sheet, wherein the visual inspection is facilitated by the image of the select sheet displayed on the display; and, either (i) reclassifying the select sheet, based on the visual inspection, as acceptable, wherein the select sheet is then added to the population of acceptable sheets; or, (ii) classifying the select sheet, based on the visual inspection, as a defective, wherein the select sheet is then added to a population of defective sheets.

We claim:

1. A method of manufacturing a chemical mechanical polishing pad having a polishing layer, comprising:
   providing a cured cake formed from a curable material; wherein the curable material comprises a liquid prepolymer and a plurality of microelements, wherein the plurality of microelements dispersed in the liquid prepolymer;

skiving the cured cake to form a plurality of skived sheets;

providing an automated inspection system, comprising:
   a magazine;
   a light source, which emits a beam;
   a light detector;
   a digital image data acquisition device; and,
   an image data processing unit;

loading the plurality of skived sheets into the magazine;

conveying the plurality of skived sheets, one skived sheet at a time, between the light source and the light detector; wherein the each skived sheet has a thickness, $T_S$, between a transmission surface and an impinging surface thereof; wherein the transmission surface and the impinging surface are substantially parallel;

wherein the beam emitted from the light source is oriented to impinge on the impinging surface; and, wherein the light detector is oriented to detect a transmitted light from the beam that is transmitted through the thickness, $T_S$, and out the transmission surface;

wherein the transmitted light has at least one detectable property;

wherein the at least one detectable property includes an intensity of the transmitted light;

wherein the intensity of the transmitted light is converted into an electrical signal by the light detector;

wherein the electrical signal from the light detector is converted into a digital signal by the digital image data acquisition device;

wherein the digital signal from the digital image data acquisition device is processed by the image data processing unit, wherein the image data processing unit is configured to detect macro inhomogeneities and to classify skived sheets as either acceptable or suspect;

wherein the plurality of skived sheets is divided into a population of acceptable sheets and a population of suspect sheets;

wherein the population of acceptable sheets includes at least one acceptable sheet; and, processing an acceptable sheet from the population of acceptable sheets to form the polishing layer of the chemical mechanical polishing pad; wherein the polishing layer is adapted for polishing a substrate.

2. The method of claim 1, wherein the population of suspect sheets includes at least one suspect sheet; wherein the at least one suspect sheet contains at least one detected macro inhomogeneity; and, wherein the image data processing unit is further configured to produce a and store in a nonvolatile memory a map of the at least one suspect sheet, wherein a location for the at least one detected macro inhomogeneity is positioned.

3. The method of claim 2, further comprising:
   choosing a select sheet from the population of suspect sheets.

4. The method of claim 3, wherein the automated inspection system, further comprises:
   a display;
   wherein an image of the select sheet is displayed on the display.

5. The method of claim 4, further comprising:
   performing a visual inspection of the select sheet, wherein the visual inspection is facilitated by the image of the select sheet displayed on the display; and,
   either (i) reclassifying the select sheet, based on the visual inspection, as acceptable, wherein the select sheet is then added to the population of acceptable sheets; or, (ii) classifying the select sheet, based on the visual inspection, as a defective, wherein the select sheet is then added to a population of defective sheets.

6. The method of claim 4, wherein the image of the select sheet is a partial image showing a magnification of at least one detected macro inhomogeneity.

7. The method of claim 6, further comprising:
   performing a visual inspection of the select sheet, wherein the visual inspection is facilitated by the image of the select sheet displayed on the display; and,
   either (i) reclassifying the select sheet, based on the visual inspection, as acceptable, wherein the select sheet is then added to the population of acceptable sheets; or, (ii) classifying the select sheet, based on the visual inspection, as a defective, wherein the select sheet is then added to a population of defective sheets.

8. The method of claim 1, wherein processing the acceptable sheet, comprises:
   forming a polishing surface by machining at least one groove into the acceptable sheet to form a groove pattern;
   wherein the groove pattern is adapted for polishing the substrate.

9. The method of claim 8, wherein processing the acceptable sheet, further comprises:
   providing a subpad;
   providing an adhesive; and,
   laminating the subpad to the acceptable sheet using the adhesive.

* * * * *